(12) United States Patent
Hossner et al.

(10) Patent No.: US 9,657,011 B2
(45) Date of Patent: May 23, 2017

(54) CHEMICAL PROCESS

(71) Applicant: GLAXO GROUP LIMITED, Brentford, Middlesex (GB)

(72) Inventors: Frank Hossner, Brentford (GB); John Bryce Strachan, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/996,306

(22) Filed: Jan. 15, 2016

(65) Prior Publication Data

US 2016/0159786 A1 Jun. 9, 2016

Related U.S. Application Data

(63) Continuation of application No. 14/421,266, filed as application No. PCT/EP2013/067035 on Aug. 14, 2013, now Pat. No. 9,273,001.

(60) Provisional application No. 61/683,369, filed on Aug. 15, 2012.

(51) Int. Cl.
  *C07D 453/00* (2006.01)
  *C07D 453/02* (2006.01)
  *C07D 211/62* (2006.01)

(52) U.S. Cl.
  CPC .......... *C07D 453/02* (2013.01); *C07D 211/62* (2013.01)

(58) Field of Classification Search
  CPC .................................................... C07D 453/00
  USPC ........................................................... 546/133
  See application file for complete search history.

(56) References Cited

U.S. PATENT DOCUMENTS 4,540,780 A    9/1985    Downs

FOREIGN PATENT DOCUMENTS

WO    2005/104745    11/2005
WO    2011/029896    3/2011

OTHER PUBLICATIONS

Laine et al., Journal of Medicinal Chemistry (2009), 52(8), 2493-2505.*
Laine, et al., Discovery of Novel 1-Azoniabicyclo[2.2.2]octane Muscarinic Acetylcholine Receptor Antagonists, Journal of Medicinal Chemistry (2009) 52(8):2493-2505.

* cited by examiner

*Primary Examiner* — Niloofar Rahmani
(74) *Attorney, Agent, or Firm* — James P Riek; R Steve Thomas

(57) ABSTRACT

The present invention relates to a process for the preparation of umeclidinium bromide, and to processes for preparing intermediates used in the preparation of umeclidinium bromide.

21 Claims, 8 Drawing Sheets

CHEMICAL PROCESS

This application is a Continuation of U.S. application Ser. No. 14/421,266 filed Feb. 12, 2015, pending, which was a United States National Stage filing under 35 U.S.C. §371 of International Patent Application No. PCT/EP2013/067035 filed Aug. 14, 2013, which claims priority from U.S. Provisional Application No. 61/683,369 filed Aug. 15, 2012, each of the forgoing being specifically incorporated by reference in their entirety herein.

FIELD OF THE INVENTION

The present invention relates to a process for the preparation of umeclidinium bromide, and to processes for preparing intermediates used in the preparation of umeclidinium bromide.

BACKGROUND TO THE INVENTION

International Patent Publication Number WO 2005/104745 (Glaxo Group Limited), filed 27 Apr. 2005, discloses muscarinic acetylcholine receptor antagonists. In particular, WO 2005/104745 discloses 4-[hydroxy(diphenyl)methyl]-1-{2-[(phenylmethyl)oxy]ethyl}-1-azoniabicyclo[2.2.2]octane bromide, of formula (I), and a process for the preparation of this compound (Example 84):

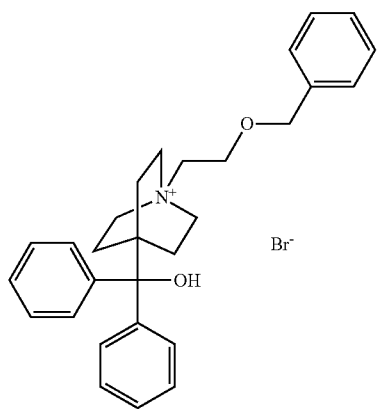

(I)

4-[Hydroxy(diphenyl)methyl]-1-{2-[(phenylmethyl)oxy]ethyl}-1-azoniabicyclo[2.2.2]octane bromide may also be referred to as umeclidinium bromide.

International Patent Publication Number WO 2011/029896 (Glaxo Group Limited), filed 10 Sep. 2010, discloses an alternative preparation for an early intermediate, ethyl-1-azabicyclo[2.2.2]octane-4-carboxylate, in the multi-step synthesis of umeclidinium bromide.

There exists a need for an alternative process for the preparation of umeclidinium bromide. In particular, a process that offers advantages over those previously disclosed in WO 2005/104745 and WO 2011/029896 is desired. Advantages may include, but are not limited to, improvements in safety, control (i.e of final product form and physical characteristics), yield, operability, handling, scalability, and efficiency.

SUMMARY OF THE INVENTION

The present invention provides, in a first aspect, a process for the preparation of umeclidinium bromide, which comprises:

a) reacting ((2-bromoethoxy)methyl)benzene, of formula (II)

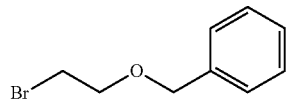

(II)

with diphenyl(quinuclidin-4-yl)methanol, of formula (III)

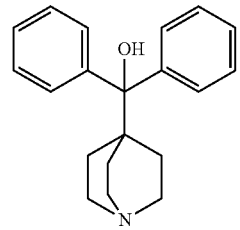

(III)

in a dipolar aprotic solvent with a boiling point greater than about 90° C. or an alcohol with a boiling point greater than about 80° C.; and optionally b) re-crystallising the product of step (a).

The present invention is further directed to intermediates used in the preparation of the compound of formula (III), and hence of umeclidinium bromide. The process disclosed herein provides a number of advantages over prior art processes of WO 2005/104745 and WO 2011/029896.

DETAILED DESCRIPTION OF THE INVENTION

Figure 1:
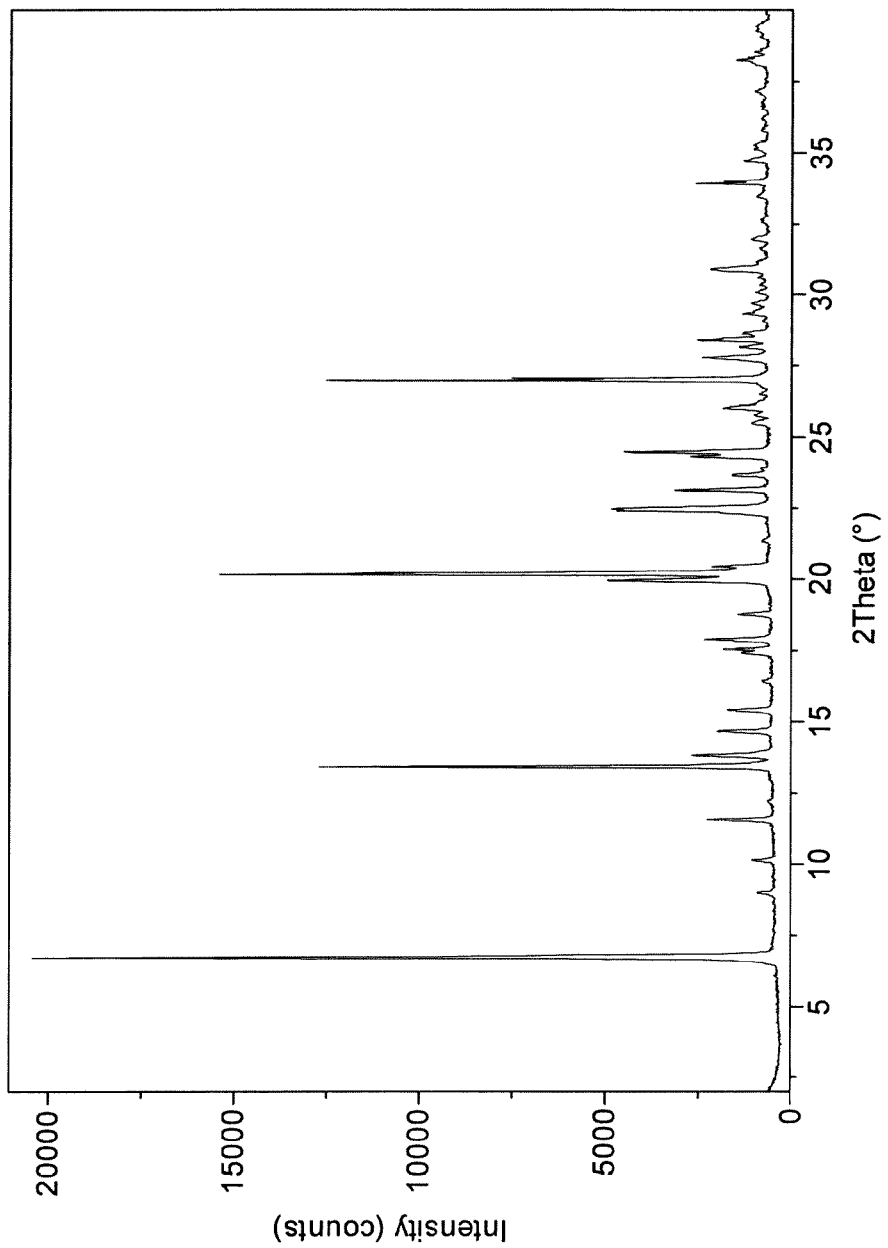
FIG. 1: XRPD data of crystalline form 1 of umeclidinium bromide as prepared by Example 8.
Figure 2:
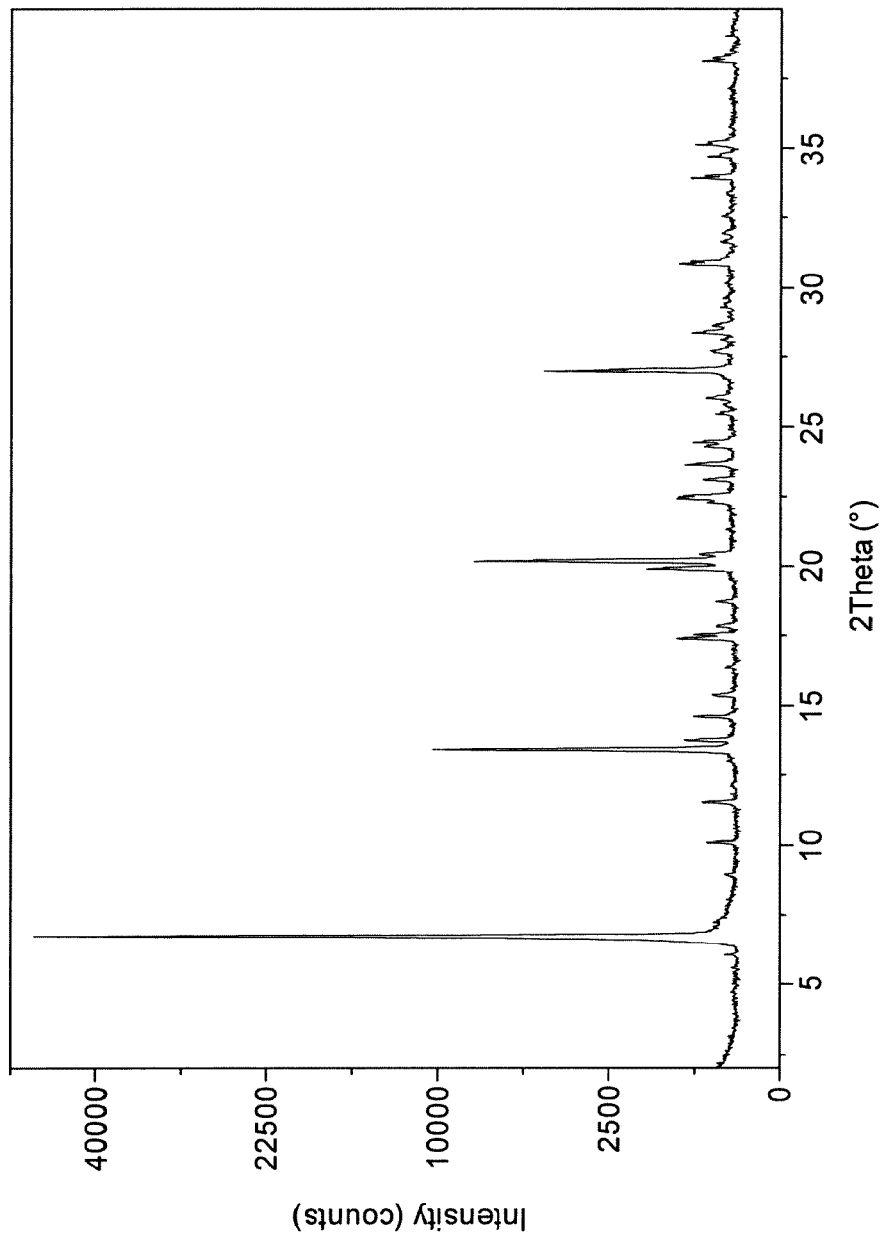
FIG. 2: XRPD data of crystalline form 1 of umeclidinium bromide as prepared by Example 7.
Figure 3:
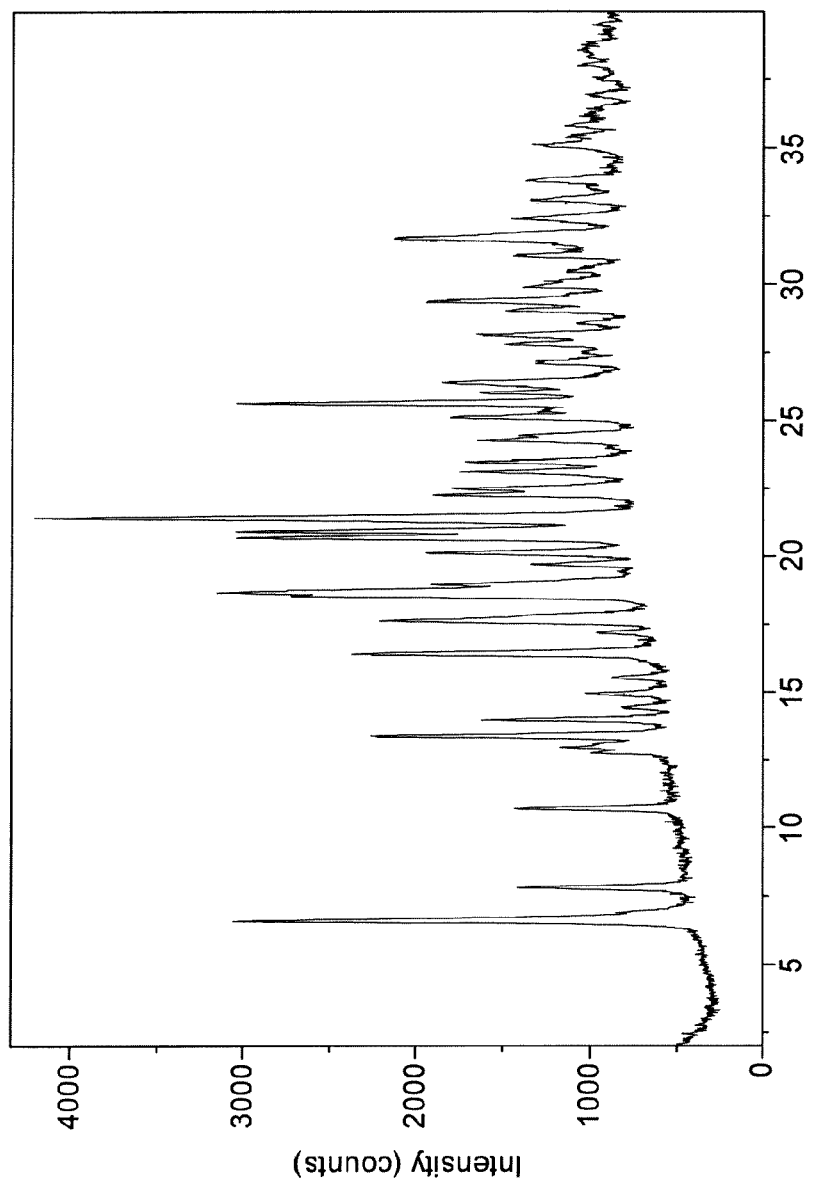
FIG. 3: XRPD data of crystalline form 2 of umeclidinium bromide as prepared by Example 9.
Figure 4:
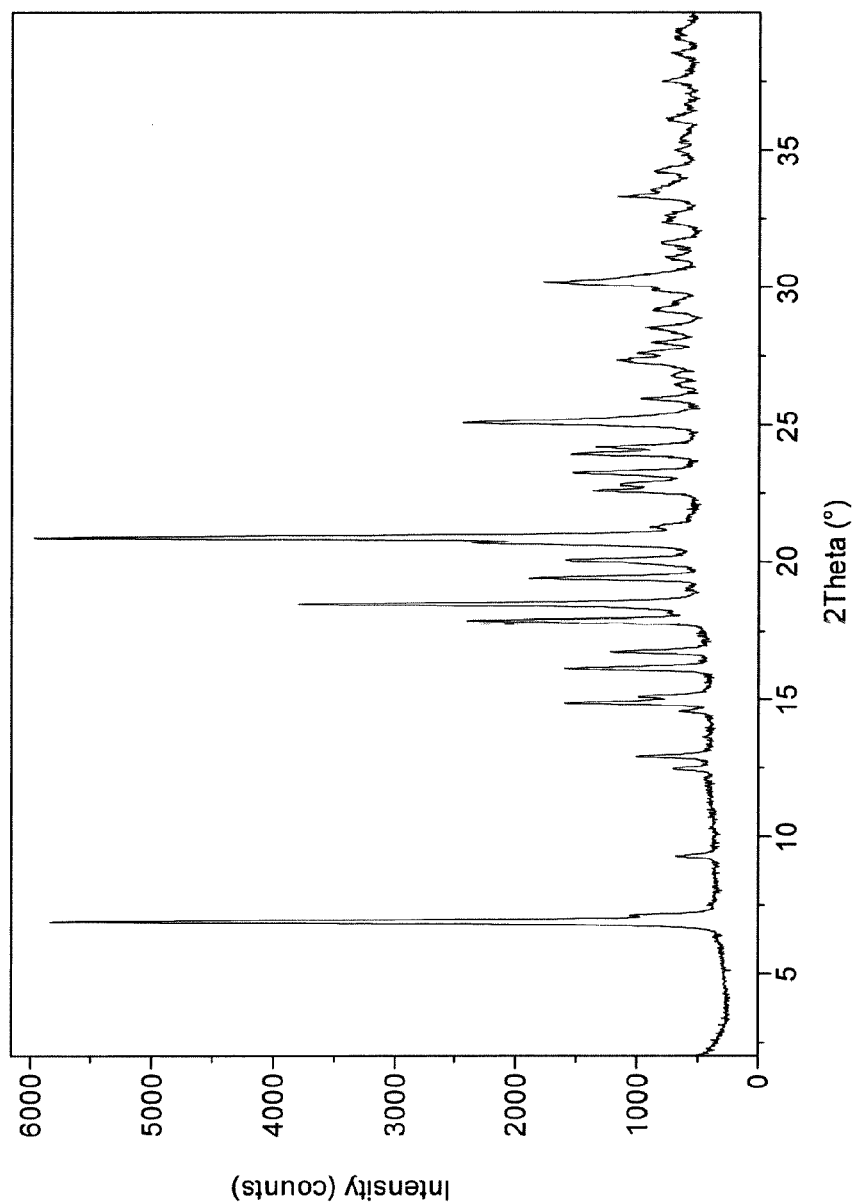
FIG. 4: XRPD data of crystalline form 3 of umeclidinium bromide as prepared by Example 10.
Figure 5:
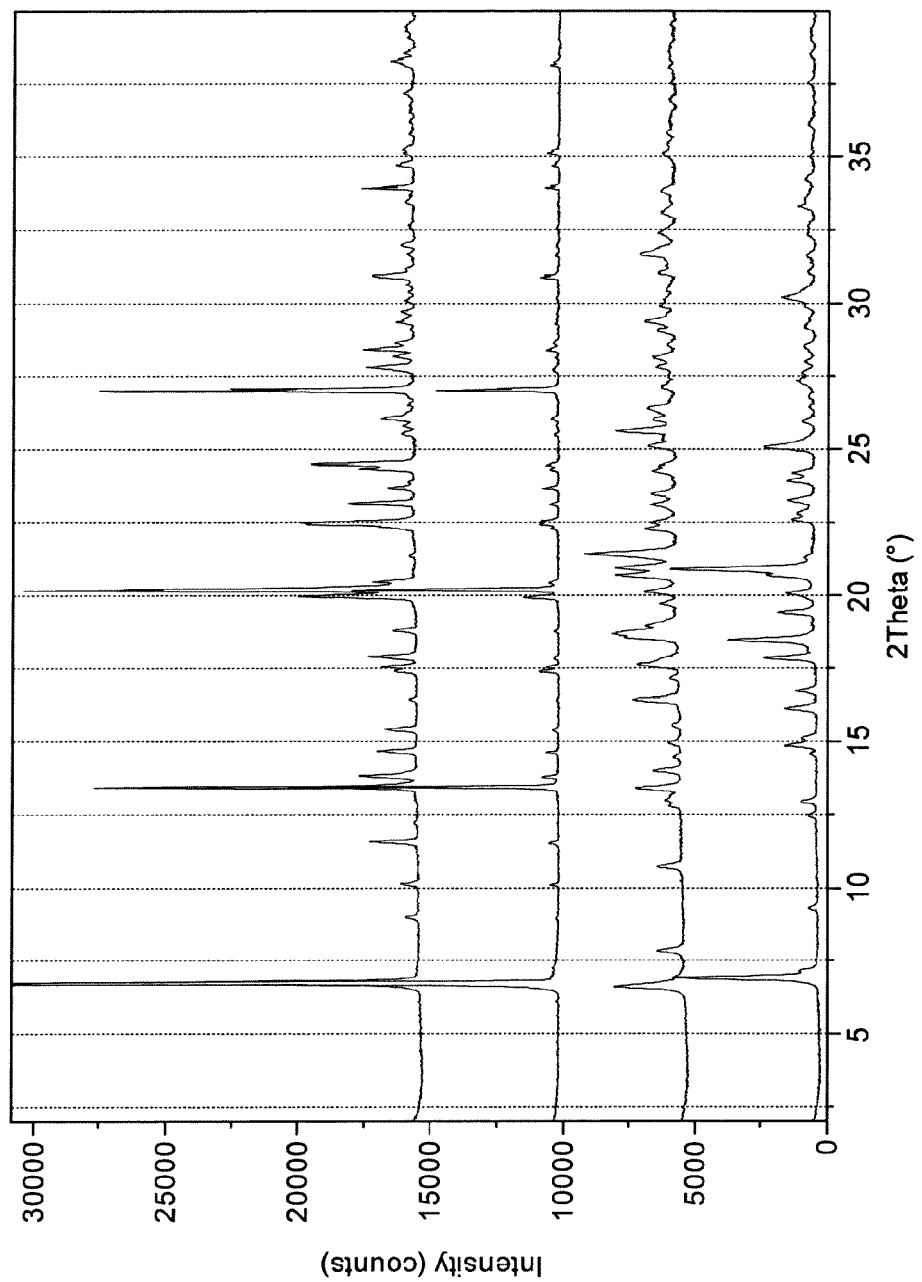
FIG. 5: Overlay of XRPD data of crystalline forms 1 (with and without seeding), 2 and 3 of umeclidinium bromide as prepared by Examples 7 to 10.

The present invention provides, in a first aspect, a process for the preparation of umeclidinium bromide, which comprises:

c) reacting ((2-bromoethoxy)methyl)benzene, of formula (II)

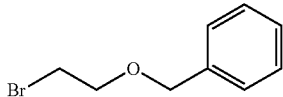

(II)

with diphenyl(quinuclidin-4-yl)methanol, of formula (III)

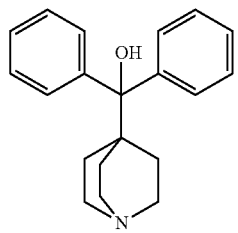

(III)

in a dipolar aprotic solvent with a boiling point greater than about 90° C. or an alcohol with a boiling point greater than about 80° C.; and optionally
d) re-crystallising the product of step (a).

In one aspect, the alcohol used in the preparation of umeclidinium bromide may be, for example, any isomer of propanol or butanol, such as n-propanol. Alternatively, the reaction may be performed in the presence of a dipolar aprotic solvent, which has a boiling point greater than 90° C., including but not limited to, DMF, DMA, DMSO or NMP.

The temperature range under which step (a) is performed may be determined based on the solubility of the compound of formula (III) in the selected solvent and the boiling point of said solvent. For example, reaction in n-propanol may be performed between approximately 60° C. and 97° C.

Umeclidinium bromide is being developed as an unsolvated version for the treatment of respiratory diseases, such as asthma and COPD. Consequently, an efficient, commercially viable process for the preparation of this version is required, which has proved challenging to deliver due to the compound's susceptibility to form solvates. To date, a number of solvates of umeclidinium bromide have been identified, including the methanol, ethanol, i-propanol, i-butanol, chlorobenzene, and p-xylene solvates. It has surprisingly been found that reacting the compound of formula (II) and (III) in n-propanol minimises the risk of solvate formation and thus removes the need for reslurries in ethyl acetate, methanol and water, which were previously required (Example 84, Method B, WO 2005/104745).

Performing the reaction in n-propanol also results in a significantly higher rate of conversion compared with the prior art process of WO 2005/104745 (43.3% vs ~90% of Example 5), and is safer due to the elimination of chloroform and acetonitrile from the process (Example 84, WO 2005/104745). In addition, reaction time has also been significantly reduced (16 hours to 3 hours in n-propanol).

The product of step (a) may be re-crystallised (step (b)) using standard procedures known in the art, such as cooling crystallisation or anti-solvent addition crystallisation. In cooling crystallisation, the reaction mixture containing dissolved product of step (a) is cooled slowly, and optionally seeded, resulting in the formation of crystals of umeclidinium bromide that will separate from the solution.

Surprisingly, the use of an aqueous n-propanol solvent mixture for re-crystallisation (by cooling crystallisation) enables robust control of the final unsolvated form and physical properties of umeclidinium bromide. In a further aspect of the invention, re-crystallisation is performed in an aqueous n-propanol solution wherein the ratio of water to n-propanol is 2:1.

After crystallisation, the crystals can be isolated by filtration, washed using a suitable solvent, such as chilled n-propanol, and dried under vacuum.

In a further aspect, the present invention provides a process for the preparation of the compound of formula (III), which process comprises reacting phenyl lithium in dibutyl ether with a compound of formula (IV)

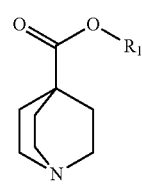

(IV)

wherein $R_1$ is $C_{1-6}$alkyl, aryl or benzyl, in a suitable solvent.

In a further aspect, the present invention provides a process for the preparation of umeclidinium bromide, which comprises preparing the compound of formula (III), comprising the step of reacting phenyl lithium in dibutyl ether with a compound of formula (IV)

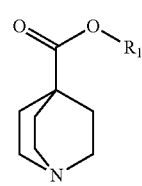

(IV)

wherein $R_1$ is $C_{1-6}$alkyl, aryl or benzyl, in a suitable solvent, and then converting the compound of formula (III) to umeclidinium bromide.

In one aspect, $R_1$ is ethyl.

As used herein, the term "alkyl" refers to a saturated hydrocarbon chain having the specified number of member atoms. For example, $C_{1-6}$alkyl refers to an alkyl group having from 1 to 6 member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, the term "aryl" refers phenyl or naphthyl. Aryl groups may be optionally substituted with one or more substituents, such as halo, $C_{1-6}$alkyl and $C_{1-6}$alkoxy.

The reaction between phenyl lithium and a compound of formula (IV) is carried out in a suitable solvent, for example an aprotic solvent such as toluene, THF, MeTHF, TBME or an alkane such as hexane and cyclohexane. In a further aspect of the invention, the reaction is performed in toluene as solvent and/or at a temperature of 0° C.

The synthesis of the compound of formula (III) outlined in WO 2005/104745 has to be operated at cryogenic temperatures (e.g. −30° C.) due to the particular reagent and solvent system used. Consequently, the process disclosed herein advantageously provides improved operability over the known process in the art, and is thus more suitable for large scale, commercial manufacture. In addition, the reaction time has been significantly reduced (for example, 16 hours to 1 hour in toluene at 0° C.).

Reaction by-products generated during the preparation of the compound of formula (III) may be removed by aqueous work-up. For example, lithium hydroxide may be removed by adding water and a polar, high-boiling, water immiscible solvent such as isomers of butanol and pentanol to the reaction mixture, heating to a suitable temperature and then performing a liquid-liquid extraction. In one aspect, the solvent is n-butanol and the temperature may be from 79 to 85° C. The realisation that inorganic by-products could be removed using a polar, high-boiling, water immiscible solvent such as n-butanol provides a further benefit in the next stage of the process, where the presence of these impurities was found, unexpectedly, to slow down the reaction. Thus, adequate removal of the inorganic by-products improves the efficiency of the process.

In a further aspect, the present invention provides a process for the preparation of the compound of formula (IV), which process comprises reacting a compound of formula (V)

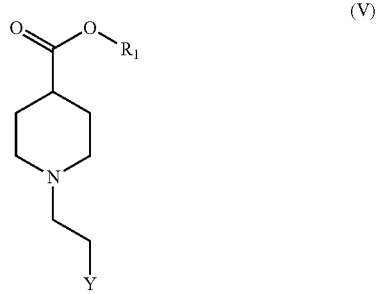

(V)

wherein $R_1$ is $C_{1-6}$alkyl, aryl or benzyl and Y is a leaving group, with a suitable base selected from KHMDS, LiHMDS and NaHMDS, in a suitable solvent.

In a further aspect, the present invention provides a process for the preparation of umeclidinium bromide, which comprises preparing the compound of formula (IV), which comprises the step of reacting a compound of formula (V)

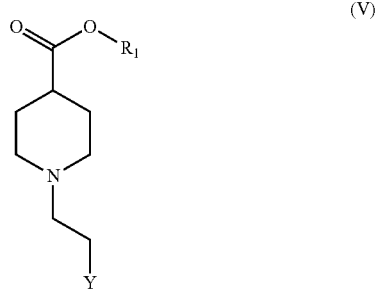

(V)

wherein $R_1$ is $C_{1-6}$alkyl, aryl or benzyl and Y is a leaving group, with a suitable base selected from KHMDS, LiH-MDS and NaHMDS, in a suitable solvent, and then converting the compound of formula (IV) to umeclidinium bromide.

In one aspect, $R_1$ is ethyl.

In one aspect, the base is KHMDS.

Example leaving groups for Y include, but are not limited to, —OTs, —OMs, —OTf, Cl or Br. In one aspect, Y is Cl.

Suitable solvents for the preparation of the compound of formula (IV) include, but are not limited to, aprotic solvents such as toluene, THF, MeTHF, TBME or alkanes such as hexane and cyclohexane. In one aspect, the solvent is toluene.

The preparation of the compound of formula (IV) outlined in WO 2005/104745 involved the reaction of the compound of formula (V) with LDA (base) in THF, and this process necessitated the use once more of cryogenic temperatures (−50° C.). The process conditions described herein surprisingly allow the reaction to be operated sufficiently at approx. 50° C. Replacement of LDA with, for example, KHMDS and a solvent switch from THF to, for example, toluene also results favourably in a reduction of the reaction time (16 hours to approximately 1 hour for the conditions outlined directly above).

In a further aspect, the present invention provides a process for the preparation of the compound of formula (V), which comprises:
a) reacting a compound of formula (VI)

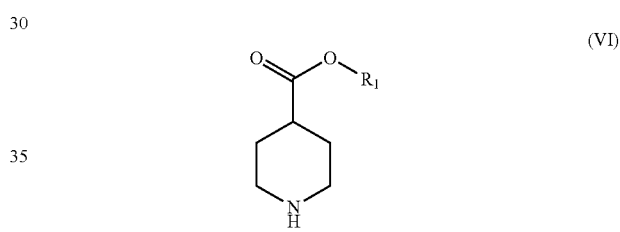

(VI)

wherein $R_1$ is $C_{1-6}$alkyl, aryl or benzyl, with a compound of formula (VII)

(VII)

wherein X is a leaving group, in the presence of a suitable base; and
b) converting the product of step (a) to the compound of formula (V) with a suitable reagent.

In a further aspect, the present invention provides a process for the preparation of umeclidinium bromide, which comprises preparing the compound of formula (V), which comprises:
a) reacting a compound of formula (VI)

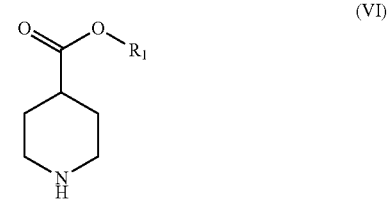

(VI)

wherein $R_1$ is $C_{1-6}$alkyl, aryl or benzyl, with a compound of formula (VII)

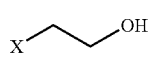

(VII)

wherein X is a leaving group, in the presence of a suitable base, and b) converting the product of step (a) to the compound of formula (V) with a suitable reagent; and then converting the compound of formula (V) to umeclidinium bromide.

In one aspect, X is Cl or Br and/or $R_1$ is ethyl.

Step (a) of the reaction is carried out in the presence of a suitable base, which includes, but is not limited to, potassium carbonate and DBU. In a further aspect of the present invention, is provided the combination of chloroethanol (X is Cl) in the presence of DBU, which provides an acceptable rate of reaction and excellent yield.

The conversion of step (b) is carried out with a suitable reagent, for example, one selected from the group consisting of thionyl chloride, sulfonyl halides, such as sulfonyl chlorides, sulfonyl anhydrides and phosphorus halides.

In one aspect, the reagent in step (b) is selected from the group consisting of thionyl chloride, p-toluenesulfonyl chloride, methanesulfonyl chloride, methanesulfonic anhydride, p-toluenesulfonic anhydride, trifluoromethanesulfonic anhydride, phosphoryl chloride, phosphorus tribromide and phosphorus pentachloride.

In yet a further aspect, the reagent is thionyl chloride.

This two-step process may advantageously provide the compound of formula (V) in a substantially higher yield than the process outlined in WO 2005/104745. For example, the process disclosed herein, using bromoethanol and potassium carbonate as reagents, provides approximately 80% conversion (see Example 1). In contrast, the process of WO 2005/104745 provides a 38.6% yield (Example 1: Ethyl 1-(2-chloroethyl)-4-piperidine carboxylate).

The low yield outlined in WO 2005/104745 is largely a result of the formation of the dimer impurity, diethyl 1,1'-(ethane-1,2-diyl)bis(piperidine-4-carboxylate), which must subsequently be separated from the compound of interest, by chromatography, increasing exposure to the highly toxic compound of formula (V). The process of the present invention eliminates the formation of this major dimer impurity, avoiding the need for a high exposure separation stage, and thus provides a much safer alternative.

WO 2011/029896 outlines an alternative method for the preparation of ethyl quinuclidine-4-carboxylate (compound of formula (IV)), via ethyl-4-(2-chloroethyl)-piperidine-4-carboxylate (Reference Example 9), which avoids the formation of the highly toxic intermediate (compound of formula (V)). However, this alternative preparation also results in very low yields (i.e 1.71-45.56% yield for the precursor to ethyl-4-(2-chloroethyl)-piperidine-4-carboxylate, Reference Example 1-7, WO 2011/029896).

Both steps in the preparation of the compound of formula (V) are conveniently carried out in the presence of a suitable solvent, such as toluene. Different solvents, or solvent mixtures, may be used for each step of the reaction.

The preparation of the compound of formula (IV) starting from the compound of formula (VI) may be performed in a series of separate reactions whereby each intermediate is isolated, or may be performed as a telescopic synthesis.

Umeclidinium bromide exists in a number of crystalline forms, which may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ss-NMR).

In one aspect, the present invention provides umeclidinium bromide in a crystalline solid state form.

In a further aspect, there is provided a crystalline solid state form of umeclidinium bromide characterised by an X-ray powder diffraction (XRPD) pattern substantially as shown in FIG. 1, 2, 3 or 4, and/or having significant diffraction peaks at 2θ values shown in Table 1.

In a further aspect, the present invention is directed to a crystalline solid state form of umeclidinium bromide, characterised by an X-ray powder diffraction pattern having diffraction peaks at 2θ values, ±0.10° 2θ experimental error, of 6.7, 8.9, 10.1, 11.5, 13.4, 13.8, 14.6, 15.4, 17.5, 17.9, 18.7, 19.9, 20.2, 22.6, 23.1, 24.3, 24.4 and/or 27.0 (Form 1).

In a further aspect, the present invention is directed to a crystalline solid state form of umeclidinium bromide, characterised by an X-ray powder diffraction pattern having diffraction peaks at 2θ values, ±0.10° 2θ experimental error, of 6.6, 7.8, 10.7, 13.4, 14.0, 14.9, 16.4, 19.7, 20.1, 20.7, 20.9, 21.4 and/or 25.6 (Form 2).

In a further aspect, the present invention is directed to a crystalline solid state form of umeclidinium bromide, characterised by an X-ray powder diffraction pattern having diffraction peaks at 2θ values, ±0.10° 2θ experimental error, of 6.9, 9.3, 12.5, 12.9, 16.1, 16.7, 17.9, 18.5, 19.4, 20.1, 20.9, 23.3 and/or 25.1 (Form 3).

The crystalline forms (Forms 1, 2 and 3) of umeclidinium bromide are further characterised by differential scanning calorimetry (DSC) traces. In a further aspect, the present invention is directed to a crystalline solid state form of umeclidinium bromide, characterised by a DSC trace with an onset temperature of approximately 236° C. (Form 1 without seeding), 232° C. (Form 2) and 232° C. (Form 3).

Experimental Section

Abbreviations

DMF: Dimethylformamide
DMA: Dimethylacetamide
DMSO: Dimethyl sulfoxide
NMP: N-methyl-2-pyrrolidone
KHMDS: Potassium bis(trimethylsilyl)amide
LDA: Lithium diisopropylamide
LiHMDS—Lithium bis(trimethylsilyl)amide
NaHMDS—Sodium bis(trimethylsilyl)amide
DBU—1,8-diazabicyclo(5.4.0)undec-7-ene
THF—Tetrahydrofuran
MeTHF—Methyl tetrahydrofuran
TBME—Methyl tert-butyl ether The invention is illustrated in the following example.

Example 1

Preparation of ethyl 1-(2-chloroethyl)-4-piperidinecarboxylate

Ethyl isonipecotate (400.1 g), potassium carbonate powder (448.7 g) and 2-bromoethanol (256 ml) in toluene (4000 ml) were heated to reflux (ca 110° C.) and stirred for 160 minutes. The reaction mixture was cooled to 60° C. and water (1200 ml) added, followed by cooling to 20° C. After stirring, the aqueous layer was separated and extracted with toluene (2000 ml). The combined organic layers were concentrated to 4200 ml by vacuum distillation. A portion of this reaction mixture (4050 ml) was heated to 50° C. and thionyl chloride (193 ml) added. After stirring for 1 hour, ethyl acetate (4600 ml) was added at 40° C. followed by ethyl 1-(2-chloroethyl)-4-piperidinecarboxylate seed (0.4 g). The slurry was aged for 35 minutes, then cooled to 20° C. and aged for 40 min. The product was filtered, washed with ethyl acetate (1500 ml) and dried under vacuum at 45° C. to give a white solid (502.7 g, 80%). EI-MS m/z 220 (M+H$^+$) Rt (2.1 min).

$^1$H NMR (400 MHz; DMSO-d6): 4.14-4.01 (4H, m), 3.57-3.42 (4H, m), 3.01 (2H, m), 2.59 (1H, m), 2.05 (2H, m), 1.88 (2H, m), 1.19 (3H, t).

Example 2

Preparation of 1-azabicyclo[2.2.2]oct-4-yl(diphenyl)methanol

Ethyl 1-(2-chloroethyl)-4-piperidinecarboxylate (199 g, for example, as prepared by Example 1) in water (800 ml) was added to toluene (2000 ml) and potassium carbonate (118 g) in water (800 ml) and rinsed in with water (400 ml). The mixture was stirred until a biphasic solution was obtained. The aqueous layer was separated and extracted with toluene (3000 ml). The combined organic layers were concentrated to 4000 ml by vacuum distillation. This solution was added to 0.5 M potassium hexamethyldisilazide in toluene (1700 ml) and toluene (2000 ml) at 40° C. Acetic acid (178 ml) was added, the mixture concentrated to 4000 ml by vacuum distillation and added to an 18% w/w aqueous potassium carbonate solution (2432 g). The layers were separated, the organic layer was concentrated to 3000 ml by vacuum distillation and toluene (1000 ml) added. The solution was cooled to −15° C. and 2M phenyl lithium in dibutyl ether (800 ml) added. Water (2000 ml) and n-butanol (700 ml) were added and the mixture heated to 75° C. The aqueous layer was removed and the organic layer washed with water (1000 ml). Toluene (1000 ml) was added and mixture distilled until 3000 ml of solvent had been removed, then cooled to 20° C. and stirred overnight. The product was filtered, washed with toluene (2×200 ml) and dried under vacuum at 40° C. to give a white solid (131 g, 57%). EI-MS m/z 294 (M+H$^+$) Rt (3.6 min).

$^1$H NMR (400 MHz; MeOD): 7.55 (4H, m), 7.27 (4H, m), 7.18 (2H, m), 2.84 (6H, m), 1.83 (6H, m).

Example 3

Preparation of 1-azabicyclo[2.2.2]oct-4-yl(diphenyl)methanol

Ethyl isonipecotate (300 g), potassium carbonate powder (330 g) and 2-bromoethanol (150 ml) in toluene (2700 ml) were refluxed under Dean & Stark conditions for 4 hours. The reaction mixture was cooled to 20° C. and water (900 ml) added. After stirring, the aqueous layer was separated and extracted with toluene (1500 ml). The combined organic layers were concentrated to 2700 ml by vacuum distillation. The reaction mixture was heated to 60° C. and thionyl chloride (150 ml) added. After stirring for 90 min the mixture was cooled to 20° C., stirred for 30 min and toluene (1800 ml) added. Water (900 ml) and 26% w/w aqueous potassium carbonate (2028 g) were added. The layers were separated and the aqueous layer extracted with toluene (7500 ml). The combined organic layers were washed with water (300 ml) and dried by addition of toluene (3000 ml) and concentration to 4800 ml by vacuum distillation. 0.5 M Potassium hexamethyldisilazide in toluene (4200 ml) was added at 40° C. and the mixture stirred for 1 hour. Ethanol (192 ml) and acetic acid (426 ml) were added and the mixture stirred at 40° C. for 2 hours. A 26% w/w aqueous potassium carbonate solution (4038 g) was added and the layers separated. The aqueous layer was extracted with toluene (2500 ml). The combined organic layers were washed with water (300 ml) and concentrated to 4500 ml by vacuum distillation. The solution was cooled to 0-5° C. and 2M phenyl lithium in dibutyl ether (1920 ml) added. After one hour, water (1500 ml) and n-butanol (1680 ml) were added and the mixture heated to 78° C. The aqueous layer was removed and the organic layer washed with water (1500 ml). The organic phase was concentrated to 6000 ml by distillation with addition of toluene, then cooled to 20° C. and stirred overnight. The product was filtered, washed with toluene (2×600 ml) and dried under vacuum to give a white solid (300 g, 53%). EI-MS m/z 294 (M+H$^+$) Rt (3.7 min).

$^1$H NMR (400 MHz; MeOD): 7.54 (4H, m), 7.26 (4H, m), 7.17 (2H, m), 2.83 (6H, m), 1.82 (6H, m).

Example 4

Preparation of 1-azabicyclo[2.2.2]oct-4-yl(diphenyl)methanol

Ethyl isonipecotate (600 g) and DBU (600 ml) were dissolved in toluene (3000 ml) and heated to 100° C. 2-Chloroethanol (330 ml) was added over 2 hours and the mixture stirred at 109° C. for a further 4.5 hours. The temperature was adjusted to 55-65° C. and thionyl chloride (378 ml) added. After stirring for 1 hour the mixture was cooled to 30° C. and water (1800 ml) and 40% w/w aqueous potassium carbonate (3350 g) were added. The layers were separated and the aqueous layer extracted with toluene (3000 ml). The combined organic layers were washed with water (600 ml) and dried by addition of toluene (2000 ml) and concentration to 6000 ml by vacuum distillation. A solution assay showed 94% conversion from ethyl isonipecotate. 0.5M Potassium hexamethyldisilazide in toluene (8400 ml) was added at 45-50° C. and the mixture stirred for 2 hours. Further 0.5M potassium hexamethyldisilazide in toluene (1260 ml) was added and the mixture stirred for 30 minutes. Ethanol (390 ml) was added and the mixture concentrated to 8400 ml by vacuum distillation. Acetic acid (850 ml) was added and the mixture stirred at 45° C. for 15 hours. A 26% w/w aqueous potassium carbonate solution (8110 g) was added and the layers separated. The aqueous layer was extracted with toluene (4800 ml). The combined organic layers were split in two halves and filtered using filter aid (38 g of Celite or Harborlite), recombined and concentrated to 6000 ml by vacuum distillation. The solution was cooled to 0-5° C. and 2M phenyl lithium in dibutyl ether (3840 ml) added. After one hour, water (3000 ml) and n-butanol (3960 ml) were added and the mixture heated to 83° C. The aqueous layer was removed and the organic layer washed with water (3000 ml). The organic phase was concentrated to 12000 ml by distillation with addition of toluene, then cooled to 20° C. and stirred overnight. The product was filtered, washed with toluene (2×1200 ml) and dried under vacuum at 70° C. to give a white solid (561 g, 50%). EI-MS m/z 294 (M+H$^+$) Rt (3.7 min).

¹H NMR (400 MHz; DMSO-d6): 7.51 (4H, m), 7.25 (4H, m), 7.15 (2H, m), 2.65 (6H, m), 1.60 (6H, m).

Example 5

Preparation of 4-[hydroxy(diphenyl)methyl]-1-{2-[(phenylmethyl)oxy]ethyl}-1-azoniabicyclo[2.2.2] octane bromide (Intermediate Grade—without seeding step)

A solution of 1-azabicyclo[2.2.2]oct-4-yl(diphenyl) methanol (31.7 kg) and benzyl 2-bromoethyl ether (25.7 kg) in n-propanol (257.5 kg) was refluxed for 13 hours. The solution was cooled to 50-55° C. over not less than an hour and stirred for 40 minutes to induce crystallisation. The slurry was cooled to 17-23° C. over not less than 1 hour and stirred for 60 minutes. The slurry was then cooled to 0-5° C. over not less than 1 hour and aged for 2 hours. The product was filtered and washed twice with n-propanol (34.8 kg and 33.8 kg). Drying under vacuum at 50° C. gave a white solid (47.95 kg, 87%).

Example 6

Preparation of 4-[hydroxy(diphenyl)methyl]-1-{2 [(phenylmethyl)oxy]ethyl}-1-azoniabicyclo[2.2.2] octane bromide (Intermediate Grade)

A solution of 1-azabicyclo[2.2.2]oct-4-yl(diphenyl) methanol (445.6 g, for example, as prepared by Example 4) and benzyl 2-bromoethyl ether (360.9 g) in n-propanol (4456 ml) was refluxed for 3 hours. The solution was cooled to 87° C., seeded with umeclidinium bromide (Form 1)(0.44 g), cooled further to 82° C. and aged for 1 hour. The slurry was cooled to 0-5° C. over 2.5 hours and aged for 1 hour. The product was filtered and washed with n-propanol (2×900 ml). Drying under vacuum at 50° C. gave a white solid (690 g, 89%). EI-MS m/z 428 (M⁺) Rt (4.7 min).
¹H NMR (400 MHz; DMSO-d6): 7.57 (4H, d), 7.40-7.30 (9H, m), 7.26 (2H, t), 5.94 (1H, s), 4.52 (2H, s), 3.84 (2H, m), 3.49 (6H, t), 3.38 (2H, m), 2.02 (6H, t).

Example 7

Preparation of crystalline form 1 of 4-[hydroxy (diphenyl)methyl]-1-{2-[(phenylmethyl)oxy]ethyl}-1-azoniabicyclo[2.2.2]octane bromide 4-[Hydroxy(diphenyl)methyl]-1-{2-[(phenylmethyl)oxy] ethyl}-1-azoniabicyclo[2.2.2]octane bromide (165 g) was dissolved in n-propanol (495 ml) and water (990 ml) at 80° C. The resulting solution was cooled to 50° C., Form 1 seed (0.825 g) in n-propanol (2.8 ml) added and rinsed in with further n-propanol (5.5 ml). After aging for one hour at 50° C., the slurry was cooled to 40° C. over 80 min, then cooled further to 0-5° C. over 105 min. The slurry sample was aged for 3 hours at 0-5° C., filtered and the product washed with n-propanol (2×330 ml). Vacuum drying at 60° C. yielded a white solid (146 g, 88%). Characterised by XRPD (see FIG. 2 and Table 1).

Example 8

Preparation of crystalline form 1 of 4-[hydroxy (diphenyl)methyl]-1-{2-[(phenylmethyl)oxy]ethyl}-1-azoniabicyclo[2.2.2]octane bromide (alternative to Example 6, without seeding step)

Figure 6:
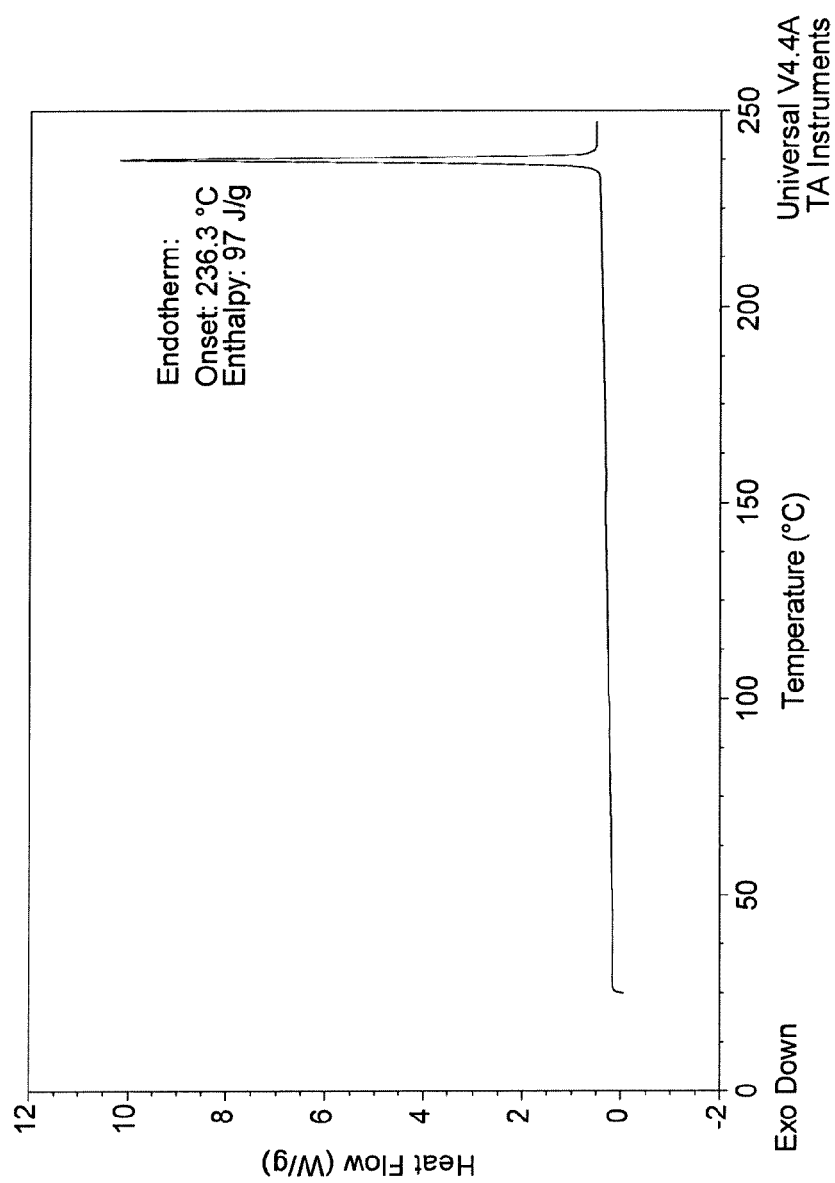
FIG. 6: DSC thermogram of crystalline form 1 of umeclidinium bromide as prepared by Example 8.

4-[Hydroxy(diphenyl)methyl]-1-{2-[(phenylmethyl)oxy] ethyl}-1-azoniabicyclo[2.2.2]octane bromide (20 g) was dissolved in n-propanol (60 ml) and water (120 ml) at 80° C. and clarified. The resulting solution was cooled to 45° C. and aged for 2 hours. A thick slurry formed, which was cooled to 0-5° C. over 3 hours. The slurry sample was aged for 1 hour at 0-5° C., filtered and the product washed with n-propanol (2×40 ml). Vacuum drying at 50° C. yielded a white solid (16 g, 80%). Characterised by XRPD (see FIG. 1 and Table 1) and DSC (see FIG. 6).

Example 9

Figure 7:
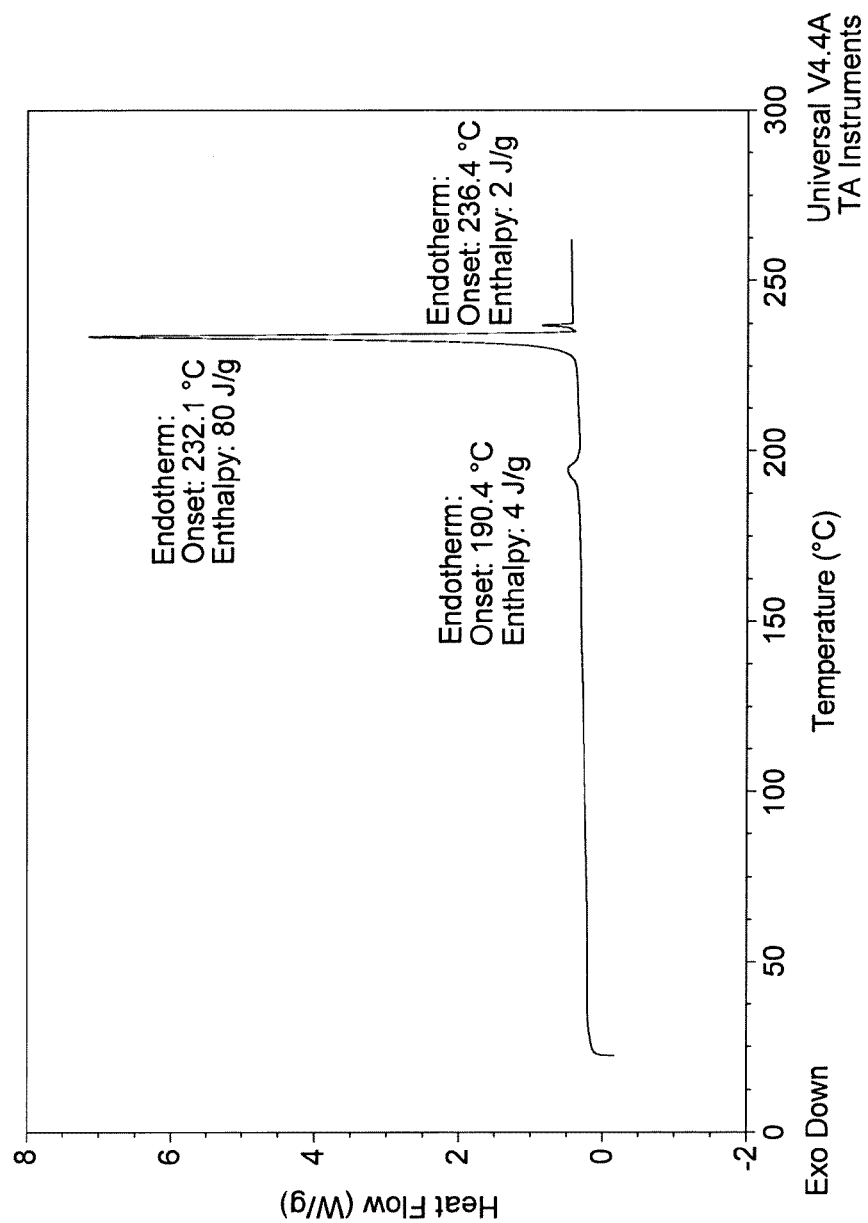
FIG. 7: DSC thermogram of crystalline form 2 of umeclidinium bromide as prepared by Example 9.

Preparation of crystalline form 2 of 4-[hydroxy (diphenyl)methyl]-1-{2-[(phenylmethyl)oxy]ethyl}-1-azoniabicyclo[2.2.2]octane bromide Nitromethane (105 ml) and n-propanol (45 ml) were added to 4-[hydroxy(diphenyl)methyl]-1-{2-[(phenylmethyl)oxy]ethyl}-1-azoniabicyclo[2.2.2]octane bromide (6 g) at 21° C. The resulting mixture was stirred at room temperature (ca 21° C.) for 30.5 hours. The cloudy mixture was filtered under gravity using a glass funnel and filter paper. The clear solution was placed under vacuum on a rotary evaporator (6-7 mbar) for 15 minutes and the resulting white solid was vacuum dried at 50° C. Yield: 5.8 g (97%). Characterised by XRPD (see FIG. 3 and Table 1) and DSC (see FIG. 7).

Example 10

Figure 8:
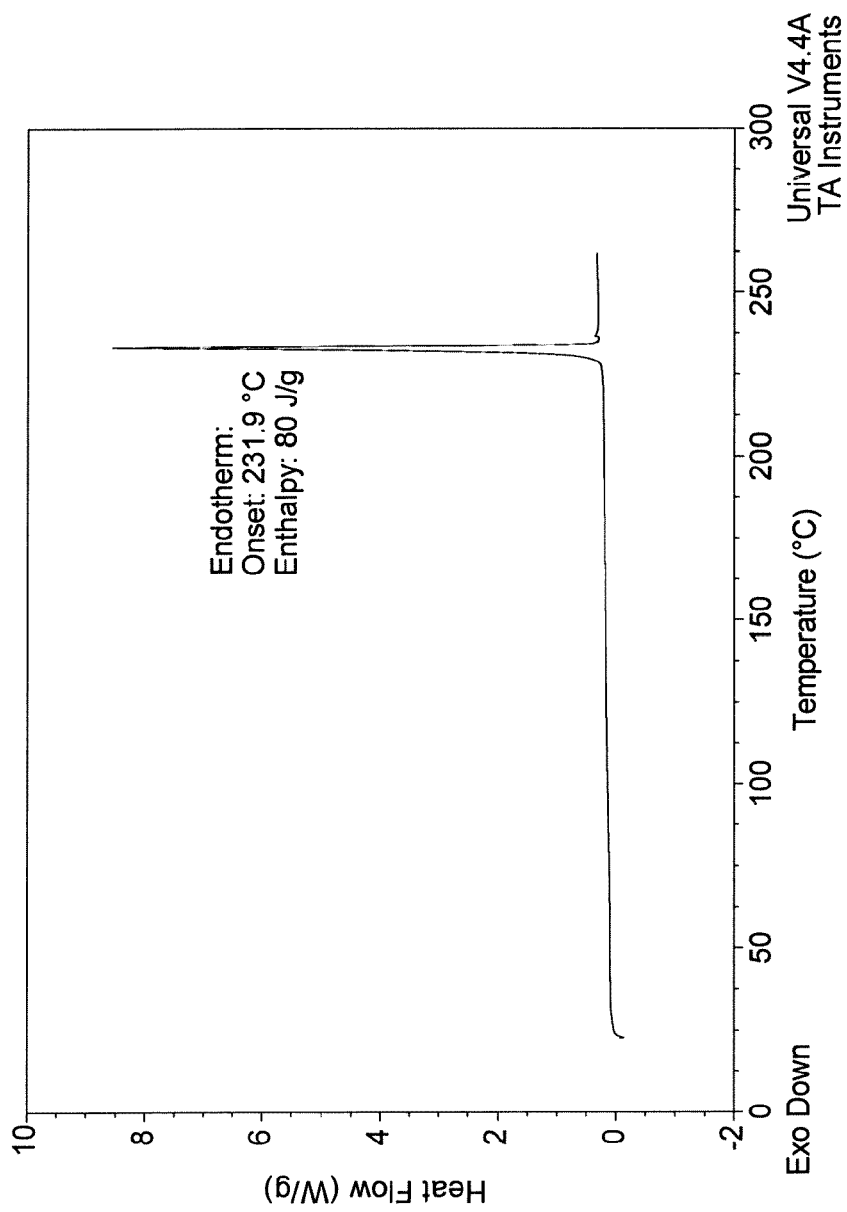
FIG. 8: DSC thermogram of crystalline form 3 of umeclidinium bromide as prepared by Example 10.

Preparation of crystalline form 3 of 4-[hydroxy (diphenyl)methyl]-1-{2-[(phenylmethyl)oxy]ethyl}-1-azoniabicyclo[2.2.2]octane bromide Dichloromethane (105 ml) and 1-pentanol (45 ml) were added to 4-[hydroxy(diphenyl)methyl]-1-{2-[(phenylmethyl)oxy]ethyl}-1-azoniabicyclo[2.2.2]octane bromide (6 g) at 21° C. The resulting mixture was stirred at room temperature (ca 21° C.) for 30 hours. The cloudy mixture was filtered under gravity using a glass funnel and filter paper. The clear solution was placed under vacuum on a rotary evaporator (6-7 mbar) for 20 minutes until a suspension was obtained. The white solid was collected under filtration and vacuum dried at 50° C. Yield: 5.1 g (85%). Characterised by XRPD (see FIG. 4 and Table 1) and DSC (see FIG. 8).

Instrument Parameters
 LC-MS Experimental Conditions
 Column: 5 cm×2.1 mm, 3 μm, Luna (C18)
 Mobile Phase: Water/Acetonitrile+0.05% v/v TFA.
 0% to 95% Acetonitrile over 8 mins.
 Total Run Time: 10 minutes.
 Flow Rate: 1.0 ml/min
 Column Temperature: 40° C.
 Mass Range: 100 to 1000 Da
 Wavelength Range: 205 to 400 nm
  ¹H NMR
  ¹H NMR spectra were recorded on a Bruker DPX400, 400 MHz instrument in either MeOD or DMSO-d6.
  X-Ray Powder Diffraction (XRPD)
 XRPD data were acquired on a PANalytical X'Pert Pro powder diffractometer, equipped with an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ. The time per step was 31.750 s. The sample was prepared by mounting a few milligrams of sample on a zero background Si wafer resulting in a thin layer of powder. Characteristic peak positions and corresponding d-spacings are summarised in Table 1. These were calculated from the raw data using PANalytical HighScore software. The experimental error in the peak positions is approximately ±0.10° 2θ. Relative peak intensities will vary due to preferred orientation, and are consequently not recorded.

TABLE 1

Characteristic XRPD peak positions for three solid state forms of umeclidinium bromide. Peaks highlighted (bold*) are unique to each form.

| Form 1 Without seeding | | Form 1 with seeding | | Form 2 | | Form 3 | |
|---|---|---|---|---|---|---|---|
| 2θ/* | d-spacing/Å | 2θ/* | d-spacing/Å | 2θ/* | d-spacing/Å | 2θ/* | d-spacing/Å |
| 6.7 | 13.2 | 6.7 | 13.1 | 6.6 | 13.4 | 6.9 | 12.8 |
| 9.0* | 9.8* | 8.9* | 9.9* | 7.8* | 11.3* | 9.3 | 9.5 |
| 10.1* | 8.7* | 10.1* | 8.8* | 10.7* | 8.3* | 12.5 | 7.1 |
| 11.6* | 7.6* | 11.5* | 7.7* | 13.4 | 6.6 | 12.9 | 6.8 |
| 13.4 | 6.6 | 13.4 | 6.6 | 14.0 | 6.3 | 16.1* | 5.5* |
| 13.8 | 6.4 | 13.8 | 6.4 | 14.9 | 5.9 | 16.7 | 5.3 |
| 14.7* | 6.0* | 14.6* | 6.1* | 16.4 | 5.4 | 17.9 | 5.0 |
| 15.4 | 5.7 | 15.4 | 5.8 | 19.7 | 4.5 | 18.5 | 4.8 |
| 17.6 | 5.0 | 17.5 | 5.1 | 20.1 | 4.4 | 19.4* | 4.6* |
| 17.9 | 5.0 | 17.9 | 5.0 | 20.7 | 4.3 | 20.1 | 4.4 |
| 18.8 | 4.7 | 18.7 | 4.7 | 20.9 | 4.2 | 20.9 | 4.3 |
| 19.9 | 4.5 | 19.9 | 4.5 | 21.4 | 4.1 | 23.3 | 3.8 |
| 20.2 | 4.4 | 20.2 | 4.4 | 25.6 | 3.5 | 25.1 | 3.6 |
| 22.5 | 4.0 | 22.6 | 3.9 | — | — | — | — |
| 23.2 | 3.8 | 23.1 | 3.8 | — | — | — | — |
| 24.3 | 3.7 | 24.3 | 3.7 | — | — | — | — |
| 24.5 | 3.6 | 24.4 | 3.6 | — | — | — | — |
| 27.0 | 3.3 | 27.0 | 3.3 | — | — | — | — |

Differential Scanning Calorimetry (DSC)

The DSC thermogram were obtained using a TA Instruments Q2000 calorimeter. The sample was weighed into an aluminium pan; a pan lid placed on top and was lightly crimped without sealing the pan. The experiment was conducted using a heating rate of 10° C. min$^{-1}$.

The invention claimed is:

1. A process for the preparation of umeclidinium bromide, which comprises:
    a) reacting ((2-bromoethoxy)methyl)benzene, of formula (II)

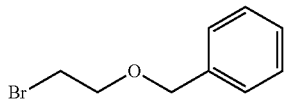

(II)

with diphenyl(quinuclidin-4-yl)methanol, of formula (III)

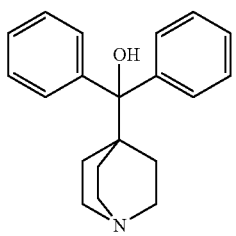

(III)

in a dipolar aprotic solvent with a boiling point greater than about 90° C. or an alcohol with a boiling point greater than about 80° C.; and optionally
    b) re-crystallising the product of step (a).

2. A process according to claim 1, wherein the alcohol is n-propanol.

3. A process according to claim 1, wherein the dipolar aprotic solvent is DMF, DMA, DMSO or NMP.

4. A process according to claim 1, wherein the re-crystallisation is performed in an aqueous n-propanol solution.

5. A process according to claim 4, wherein the ratio of water to n-propanol is 2 to 1.

6. A process according to claim 1, wherein the compound of formula (III) is prepared by a process comprising reacting phenyl lithium in dibutyl ether with a compound of formula (IV)

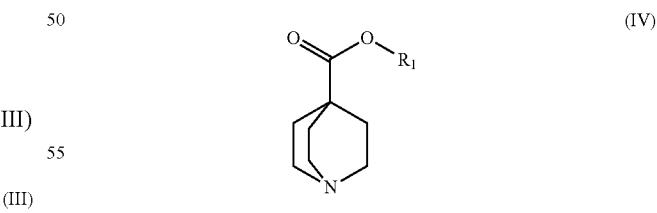

(IV)

wherein $R_1$ is $C_{1-6}$alkyl, aryl or benzyl, in a suitable solvent.

7. A process according to claim 6, wherein the solvent is toluene.

8. A process according to claim 6, wherein the compound of formula (IV) is prepared by a process comprising reacting a compound of formula (V)

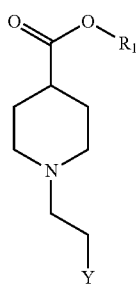

wherein $R_1$ is $C_{1-6}$alkyl, aryl or benzyl and Y is a leaving group, with a suitable base selected from KHMDS, LiHMDS and NaHMDS, in a suitable solvent.

9. A process according to claim 8, wherein Y is —OTs, —OMs, —OTf, Cl or Br.

10. A process according to claim 9, wherein Y is Cl.

11. A process according to claim 8, wherein the solvent is toluene.

12. A process according to claim 8, wherein the base is KHMDS.

13. A process according to claim 8, wherein the compound of formula (V) is prepared by a process which comprises:

a) reacting a compound of formula (VI)

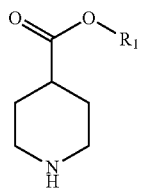

wherein $R_1$ is $C_{1-6}$ alkyl, aryl or benzyl, with a compound of formula (VII)

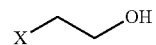

wherein X is a leaving group, in the presence of a suitable base; and b) converting the product of step (a) to the compound of formula (V) with a suitable reagent.

14. A process according to claim 13, wherein X is Cl or Br.

15. A process according to claim 13, wherein the reagent in step (b) is selected from the group consisting of thionyl chloride, sulfonyl halides, such as sulfonyl chlorides, sulfonyl anhydrides and phosphorus halides.

16. A process according to claim 13, wherein the reagent in step (b) is selected from the group consisting of thionyl chloride, p-toluenesulfonyl chloride, methanesulfonyl chloride, methanesulfonic anhydride, p-toluenesulfonic anhydride, trifluoromethanesulfonic anhydride, phosphoryl chloride, phosphorus tribromide and phosphorus pentachloride.

17. A process according to claim 15, wherein the reagent is thionyl chloride.

18. A process according to claim 13, wherein steps (a) and (b) are carried out in a suitable solvent.

19. A process according to claim 18, wherein the solvent is toluene.

20. A process according to claim 13, wherein the base is DBU.

21. A process according to claim 5, wherein $R_1$ is ethyl.

\* \* \* \* \*